(12) United States Patent
Zhang et al.

(10) Patent No.: US 9,826,927 B2
(45) Date of Patent: Nov. 28, 2017

(54) BLOOD LANCET DEVICE

(75) Inventors: Libo Zhang, Tianjin (CN); Chengzhe Cui, Tianjin (CN); Bing Li, Tianjin (CN)

(73) Assignee: Tianjin Huahong Technology Co., Ltd., Tianjin (CN)

( * ) Notice: Subject to any disclaimer, the term of this patent is extended or adjusted under 35 U.S.C. 154(b) by 1122 days.

(21) Appl. No.: 13/606,751

(22) Filed: Sep. 7, 2012

(65) Prior Publication Data

US 2013/0066352 A1 Mar. 14, 2013

(30) Foreign Application Priority Data

Sep. 9, 2011 (CN) .......................... 2011 1 0267827

(51) Int. Cl.
*A61B 5/151* (2006.01)
*A61B 5/15* (2006.01)

(52) U.S. Cl.
CPC ........ *A61B 5/15144* (2013.01); *A61B 5/1513* (2013.01); *A61B 5/150022* (2013.01); *A61B 5/15109* (2013.01); *A61B 5/15117* (2013.01); *A61B 5/150412* (2013.01); *A61B 5/150503* (2013.01); *A61B 5/150564* (2013.01); *A61B 5/150595* (2013.01); *A61B 5/150618* (2013.01); *A61B 5/150717* (2013.01); *A61B 5/150916* (2013.01)

(58) Field of Classification Search
CPC . A61B 5/1411; A61B 5/15144; A61B 5/1513; A61B 5/150412; A61B 5/15117; A61B 5/150503; A61B 5/150916; A61B 5/150595; A61B 5/150564; A61B 5/150717; A61B 5/15109; A61B 5/150022

See application file for complete search history.

(56) References Cited

U.S. PATENT DOCUMENTS

| | | | |
|---|---|---|---|
| 5,628,765 A * | 5/1997 | Morita | A61B 5/1411 604/136 |
| 2006/0052809 A1 * | 3/2006 | Karbowniczek | A61B 5/1411 606/181 |
| 2007/0083222 A1 * | 4/2007 | Schraga | A61B 5/1411 606/181 |
| 2007/0161960 A1 * | 7/2007 | Chen | A61B 5/1411 604/187 |

FOREIGN PATENT DOCUMENTS

| CN | 2678564 Y | 2/2005 |
|---|---|---|
| CN | 201341887 Y | 11/2009 |

* cited by examiner

*Primary Examiner* — Sarah W Aleman
*Assistant Examiner* — Rachel S Highland
(74) *Attorney, Agent, or Firm* — Knobbe, Martens, Olson & Bear, LLP

(57) ABSTRACT

A blood lancet device comprising a housing having one end formed as an opening; a sliding sleeve having one end extending from the opening to the outside of the housing; a blood lancet including a needle body and a needle tip arranged at one end of the needle body, the sliding sleeve being bushed at the outside of the housing, said blood lancet adapted to move relative to the sliding sleeve so as to expose the needle tip at the opening; and a biasing member having one end securely fixed with another end of needle body.

19 Claims, 6 Drawing Sheets

BLOOD LANCET DEVICE

CROSS-REFERENCE TO RELATED APPLICATION

This application claims the benefit of the Chinese Patent Application No. 201110267827.5 filed on Sep. 9, 2011 in the State Intellectual Property Office of China, the whole disclosure of which is incorporated herein by reference.

FIELD OF INVENTION

The present invention relates to a blood lancet device, more particularly, to a blood lancet device of which a needle is retractable after blood collection.

BACKGROUND OF INVENTION

The blood lancet device in the prior art, such as the blood lancet device disclosed in the patent documents CN2678564Y and CN201341887Y, employs an inclined surface fitting structure to guide the blood collection needle to rotate to the injection position, such a blood lancet device has a relative complicated structure, and also, the situation for piercing the blood collection needle falsely is easily occurred.

SUMMARY OF INVENTION

It is an object of the present invention to overcome or at least relieve the technical problem in the prior art.

According to a first aspect of the present invention, a blood lancet device is provided, which comprises: a housing having one end formed into an opening; a sliding sleeve adapted to slide along an axial direction of the housing inside the housing and one end thereof extending from said opening to the outside of the housing; a blood lancet including a needle body and a needle tip arranged at one end of the needle body, said blood lancet being adapted to slide relative to said sliding sleeve so as to expose the needle tip at said opening; a biasing member having one end engaged with another end of said needle body, wherein said sliding sleeve is provided with at least one slot extending toward said one end of the sliding sleeve from the other end of the sliding sleeve, said at least one slot provides the other end of said sliding sleeve with an elasticity for deforming radially and inwardly, when the sliding sleeve is in a first position within the housing, the other end of the sliding sleeve is pressed within said housing so as to elastically deform radially and inwardly, and the needle body abuts against the other end of the sliding sleeve under the action of the biasing member; when the sliding sleeve is in a second position within the housing, the other end of said sliding sleeve is not pressed inside the housing or subjects a pressing force less than the pressing force subjected at said first position and said needle body is moved toward said opening along said sliding sleeve under the action of the biasing member.

Advantageously, said at least one slot includes two guiding slots extending toward said one end of the sliding sleeve from the other end of the sliding sleeve, said two guiding slots dividing said other end of the sliding sleeve into two guiding ends being elastically deformable toward each other; said needle body further comprises two lugs arranged in opposite, two lugs are adapted to move along said two guiding slots under the action of the biasing member; guiding portions are provided inside said housing for engaging with said two guiding ends, the engagements between said guide portions and said guiding ends are adapted for pressing two guiding ends such that the width of the guiding slot at said other end of the sliding sleeve is reduced so as to prevent said two lugs from moving along said two guiding slots toward said one end of the sliding sleeve under the action of the biasing member.

Alternatively, a tip end of each guiding end has a protrusion protruded radially and outwardly; said protrusions are adapted to engage with the guide portions.

Advantageously, a recess is provided on said protrusion, and the guide portions are guide rails extending along the axial direction of said housing, and said recess is fitted with the guide rail. Further, an initial section of said guide rail that engages with said recess is formed into an inclined engaging surface.

Advantageously, said guiding portions comprise sliding slots extending in the axial direction of the housing, said protrusion is adapted to move along the sliding slots.

Advantageously, a groove extending toward said one end of the sliding sleeve from the tip end of said guiding end is provided on each guiding end, said groove divides the corresponding protrusion into a first protruding portion and a second protruding portion separated from the first protruding portion. Furthermore, a first recess portion is provided on the first protruding portion and a second recess portion is provided on the second protruding portion, said guiding portions includes a first guide rail portion and a second guide rail portion which are fitted with said first recess portion and said second recess portion, respectively and extend along the axial direction of said housing. Further, both the initial section of said first guide rail portion and the initial section of said second guide rail portion respectively engaged with said first recess portion and said second recess portion are formed into inclined engaged surfaces. Alternatively, said guiding portions comprise a first guiding slot portion and a second guiding slot portion extending along the axial direction of said housing, said first recess portion and said second recess portion are adapted to move along said first guiding slot portion and said second guiding slot portion, respectively.

Alternatively, a longitudinal rib protruded radially and outwardly is disposed at an outer surface of each of said guiding ends, said guiding portions comprise rib guiding slots extending along the axial direction of the housing, said longitudinal rib is engaged with said the corresponding rib guiding slot. Advantageously, a thickness of the longitudinal rib in the radial direction is gradually reduced in a direction from said other end of the sliding sleeve to said other end of the sliding sleeve. Alternatively, the longitudinal rid defines a distance by which said one end of the sliding sleeve moves to the outside of the opening.

Advantageously, at least one stopper is further disposed on the outer surface of said sliding sleeve, said stopper defines a distance by which said one end of the sliding sleeve moves outside the opening.

Advantageously, an end of each lug which enters said guiding slots is formed in a tapered shape narrowed toward said one end of the needle body. Furthermore, the end of each lug which enters said guiding slot is formed into said tapered shape by ways of having an inclined surface or a semi-cylindrical surface.

Advantageously, other end of the housing is provided with an end cover, said end cover is mounted at said other end of said housing, and other end of the biasing member is fixed on said end cap.

Advantageously, said blood lancet device further comprises an end cap; said blood lancet further comprises a needle tip covering element of which one end extends to the outside of the housing, wherein the internal structure of the end cap is engaged with the end of the needle tip covering element so as to cover said opening with said end cap.

Advantageously, a lug guiding member extending along the axial direction of the housing is disposed inside the housing.

Advantageously, an interference fit is existed between the opening of said housing and the outer surface of said one end of the sliding sleeve so as to prevent said one end of said sliding sleeve from sliding inside said housing. Particularly, a pawl is further provided in the vicinity of the opening inside said housing, and a pawl fitting slot is provided at the tip end of said one end of the sliding sleeve, the fit between the pawl and the pawl fitting slot prevents said one end of the sliding sleeve sliding into the inside of the housing.

Alternatively, said other end of said sliding sleeve has a boss protruded radially and outwardly; when the sliding sleeve is in the first position, an inner wall of the housing is engaged with said boss so as to press said other end of the sliding sleeve; when the sliding sleeve is in the second position, the inner wall of the housing is not engaged with said boss.

BRIEF DESCRIPTION OF THE DRAWINGS

FIG. 3a-FIG. 3f are structural views of the blood lancet device according to one embodiment of the present invention, wherein FIG. 3a is an end view of the opening end of the housing, FIG. 3b is a sectional view taken along line A-A in FIG. 3a, FIG. 3c is a sectional view taken along line B-B in FIG. 3a, FIG. 3d is an end view of the end cover side of the housing, FIG. 3e is a perspective schematic view of the housing when viewed from the end cover side, FIG. 3f is a perspective schematic view of the housing when viewed from the opening side;

DETAILED DESCRIPTION OF PREFERRED EMBODIMENTS

Figure 1A:
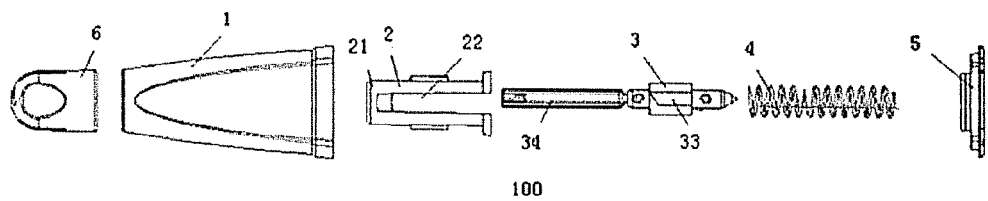
FIG. 1a and FIG. 1b are respectively exploded schematic views of the structure of a blood lancet device according to one embodiment of the present invention.

Following will be made in detail to the exemplary embodiments of the present invention, examples of which are illustrated in the accompany drawings, wherein like reference numerals refer to like elements throughout. The embodiments described by referring to the figures are exemplary, which intend to explain the present invention, but not the limitation to the present invention.

The present invention relates to a blood lancet device, comprising: a housing having one end formed as an opening; a sliding sleeve adapted to slide along an axial direction of said housing inside the housing, and one end of the sliding sleeve being extended from said opening to an outside of the housing; a blood lancet including a needle body and a needle tip disposed at one end of said needle body, said blood lancet adapted to move relative to said sliding sleeve so as to expose the needle tip at said opening; a biasing member having one end engaged with another end of the needle body, wherein, said sliding sleeve is provided with at least one slot extending toward said one end of the sliding sleeve from the other end of the sliding sleeve, said at least one slot provides the other end of said sliding sleeve with an elasticity for deforming radially and inwardly; at a first position within the housing where the sliding sleeve is located, the other end of said sliding sleeve is pressed inside said housing so as to elastically deform radially and inwardly; and at a second position within the housing where the sliding sleeve is located, the other end of the sliding sleeve is not pressed inside the housing or subjects a pressing force less than the pressing force subjected at said first position, and said needle body moves toward said opening along said sliding sleeve under the action of the biasing member.

Now, refer to FIGS. 1a, 1b and 2-5, the blood lancet device 100 according to one exemplary embodiment of the present invention comprises: a housing 1 having one end formed into an opening 11; a sliding sleeve 2 adapted to slide inside the housing along the axial direction of the housing 1; a blood lancet 3 having a needle body 31 and a needle tip 32 arranged at one end of the needle body, said blood lancet 3 adapted to move relative to the sliding sleeve 2 to expose the needle tip 32 at said opening 11; a biasing member 4 having one end securely engaged with the another end (in opposite to one end of the needle body 31, and hereafter, one end of a component and the other end of the component indicate, for example, ends of the component in opposite in a longitudinal direction) of the needle body 31, wherein: two guiding slots 22 are extendably provided toward said one end 21 of the sliding sleeve 2 from the other end of the sliding sleeve, such two guiding slots 22 divide the other end of the sliding sleeve 2 into two guiding ends 23 which are elastically deformable toward each other; the needle body 3 further comprises two lugs 33 adapted to move along two guiding slots 22 respectively under the action of the biasing member 4; guiding portions (described in detail in below) engaged with said two guiding ends are provided inside the housing 1, engagements between the guiding portions and guiding ends 23 are adapted to press two guiding ends 23 such that the width of the guiding slot 22 at the other end of the sliding sleeve 2 is reduced so as to prevent the two lugs 33 from moving toward said one end of the sliding sleeve along two guiding slots 22 under the action of the biasing member 4.

Above "securely engage" means when the biasing member 4 pushes and pulls the blood lancet, one end of the biasing member 4 will not disengage from the another end of the needle body 31. However, if another biasing member is provided adjacent to the opening for backing the needle tip into the housing after blood collection, the biasing member 4 may not have the function of pulling the needle tip back into the housing, and thus the "securely engagement" between the biasing member 4 and the needle body is unnecessary.

Here, the biasing member 4 is preferably a metal spring or a plastic spring, certainly, it also can be other elastomer adapted to provide elasticity. The engagements of the lugs 33 with the bottom of the guiding slots 22 can limit the length of the needle tip 32 of the blood lancet 3 exposed from the housing 1. FIGS. 1a, 1b, 2 and 6 show that an end cover 5 is provided at the other end of the housing 1. As the component independent from the housing 1, during the assembly, the end cover 5 is adapted to releasably install on the housing 1. The other end of the biasing member is fixed on the end cover 5, by this, the end cover 5 functions to locate the biasing member 4. Furthermore, the biasing member 4 also can be integrated fixed on the end cover.

Figure 4:
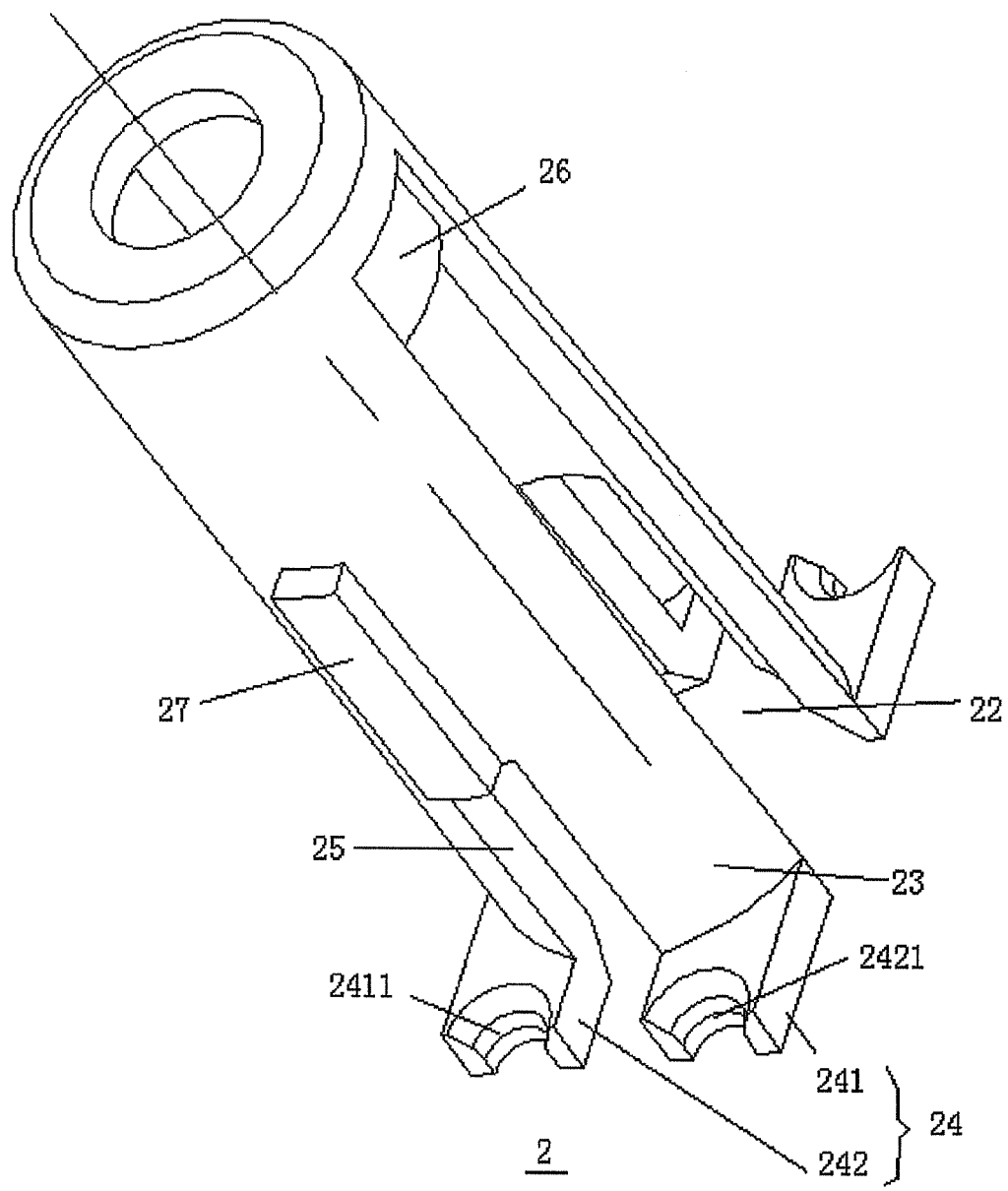
FIG. 4 is a perspective schematic view of a sliding sleeve of the blood lancet device according to one embodiment of the present invention.

As shown in FIG. 4, a tip end of each of guiding ends 23 has a protrusion 24 protruded radially and outwardly, and said protrusion 24 is adapted to engage with the corresponding guiding portion. More particularly, a groove 25 extending toward said one end 21 of the sliding sleeve 2 from the tip end of the guiding end is provided on each of guiding ends 23, said groove 25 divides the corresponding protrusion 24 into a first protruding portion 241 and a second protruding portion 242 which are separated from each other. Such a groove 25 is facilitated to keep the elastic restoring force of the guiding end 23. A first recess portion 2411 is provided on the first protruding portion 241 and a second recess portion 2421 is provided on the second protruding portion 241, the guiding portion includes a first guide rail 12 and a second guide rail 13 extending along the axial direction of the housing 1 and being fitted with the first recess portion 2411 and the second recess portion 2421, respectively. Initial sections of the first guide rail 12 and the second guide rail 13 which are respectively fitted with the first recess portion 2411 and the second recess portion 2421 are formed as inclined engaging surfaces 18, which are facilitated in the cooperation between the recess portions and the guide rails.

The first recess portion 2411 and the second recess portion 2421 may not be provided on the protrusion 24. In this case, the whole protrusion 24 is able to move in the guide slot inside the housing 1.

Alternatively, although it is not shown, the protrusion 24 also can be not divided into two protruding portions, in this case, a recess that is similar to the first recess portion 2411 in FIG. 4 is provided on the protrusion 24, correspondingly, the guiding portion inside the housing 1 includes a guide rail fitted with the recess, and advantageously, the initial section of the guide rail fitted with the recess is also formed as an inclined engaging surface. However, in the state where the protrusion 24 is not divided into two protruding portions, the guiding portion inside the housing 1 also can be the guiding slot extending along the axial direction of the housing, and such a protrusion 24 is adapted to move within the guiding slot.

In above, the particular examples, in which the protrusion protruded radially and outwardly is provided on the guiding end 23 and the protrusion is engaged with the guiding portion (the guiding slot or the guide rail) inside the housing 1, are described. But the engagement between the guiding end 23 and the guiding portion inside the housing 1 also can employ other forms. For example, a longitudinal rib protruded radially and outwardly is provided at an outer surface of each guiding end, said guiding portion is a rib guiding slot extending along the axial direction of the housing, said longitudinal rib is adapted to engage with the rid guiding slot. Advantageously, the thickness of the longitudinal rib in a radially direction is gradually reduced in a direction from the other end of the sliding sleeve to said one side of the sliding sleeve. Advantageously, said longitudinal rib can directly define a distance by which the one end 21 of the sliding sleeve 2 move to the outside of the opening 11. Further, for example, there can be no rib or protrusion provided on the guiding end 23 and a part of the inner wall of the housing 1 serves as a guiding portion, at this time, the guiding portion directly presses the outer wall of the guiding end 23 to reduce the width of the guiding slot 22 at said other end of the sliding sleeve.

Figure 5:
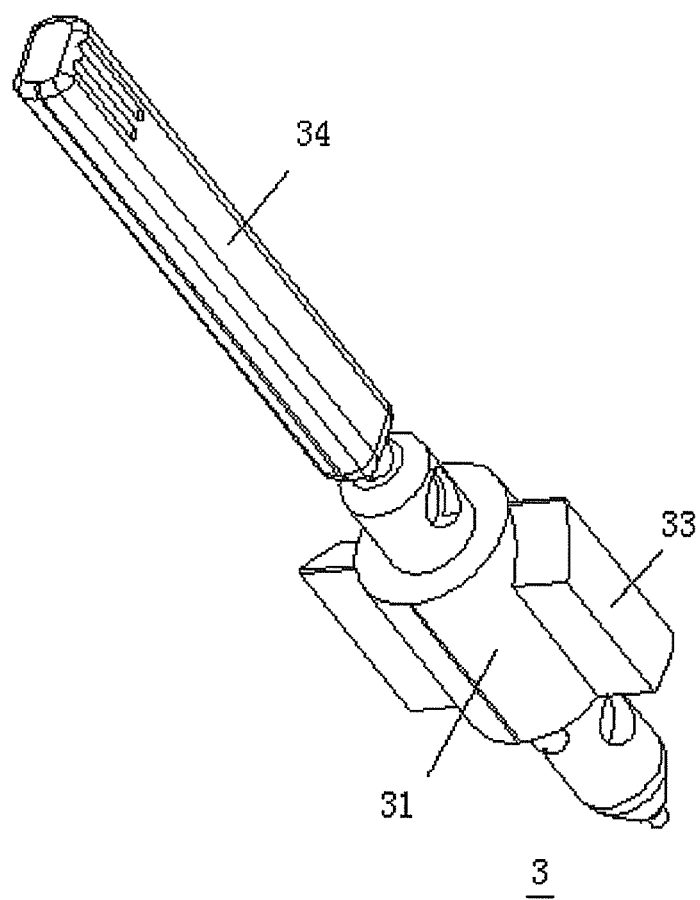
FIG. 5 is a perspective schematic view of a blood lancet of the blood lancet device according to one embodiment of the present invention.

As shown in FIG. 5, the end of each lug 33 which enters the sliding slot 22 has a tapered shape which is narrowed toward the one end of the needle body 31, for example, the tapered shape is formed with an inclined surface; however, the end of the lug 33 also can provide with two inclined surfaces to form the tapered shape. In addition, the end of the lug 33 can have a tapered shape by ways of having a semi-cylindrical surface. By using such a tapered shape, it is facilitated in that the lug 33 can be easily entered within the guiding slot 22 when the engagement between the guiding end 23 of the sliding sleeve 2 and the guiding portion inside the housing 1 is disengaged.

Figure 3A:
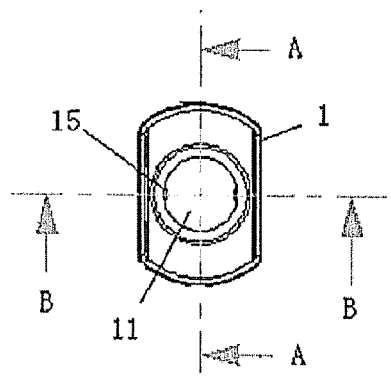
Figure 3B:
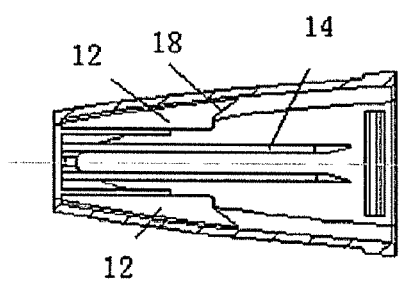
Figure 3C:
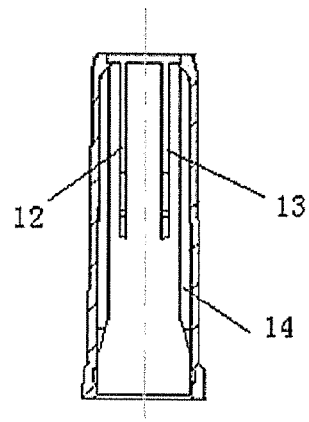
Figure 3E:
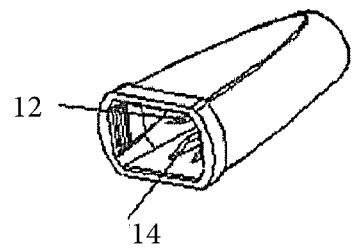
Figure 3D:
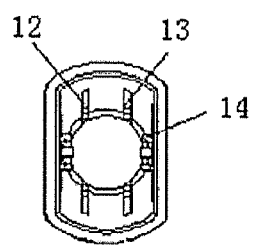
Figure 3F:
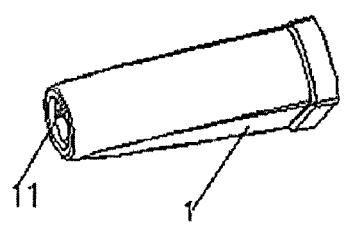

Referring to FIGS. 3d, 3e, a lug guiding member 14 extending along the axial direction of the housing 1 is also provided inside the housing 1, such a lug guiding member may be in the form of the guiding rid or guiding slot. The lug guiding member 14 not only facilitates to guide the lug moving along the housing longitudinally but also ensures the lug 33 is aligned with the guiding slot 22. In the housing 1, in the state where both the lug guiding member 14 and the guiding portion are the guide rail or guiding rib, the longitudinal length of the lug guiding member 14 is greater than the longitudinal length of the guiding portion, this will help the blood lancet 3 being easily assembled in the housing.

Advantageously, an interference fit is existed between the opening 11 of the housing 1 and the outer surface of the one end 21 of the sliding sleeve, so as to prevent said one end 21 of the sliding sleeve 2 from sliding into the inside of the housing 1. Such a design facilitates to prevent the needle 32 from exposing or being easily viewed from the opening 11 after the blood lancet device is used. As shown in FIG. 3a, a pawl 15 is provided in the vicinity of the opening 11 inside the housing 1, refer to FIG. 4, the tip end of the one end 21 of is the sliding sleeve 2 is provided with a pawl fitting slot 26, the fitting between the pawl 15 and the pawl fitting slot 26 prevents said one end of the sliding sleeve from sliding into the inside of the housing. However, in order to be easy to allow one end 21 of the sliding sleeve 2 to pass through the opening 11 during the assembly, the pawl 15 can be formed with an inclined surface over which said one end 21 of the sliding sleeve 2 can be easy to slide, and an end surface of the pawl 15 for blocking one end 21 of the sliding sleeve 2 from sliding into the housing 1 is radially perpendicular to the inner surface of the sliding sleeve 2.

As shown in FIG. 4, the outer surface of the sliding sleeve 2 further provides with at least one stopper 27, said stopper 27 defines a distance by which one end 21 of the sliding sleeve 2 moves to the outside of the opening 11. That is, the stopper 27 also prevents the sliding sleeve 2 from completely sliding out of the housing 1.

Figure 1B:
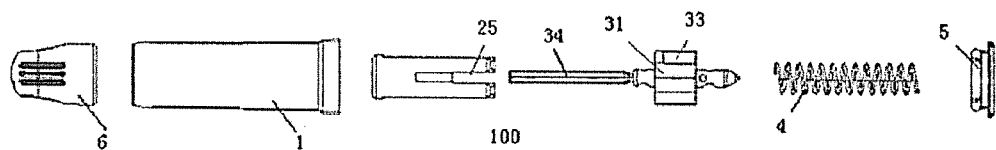
Figure 2:
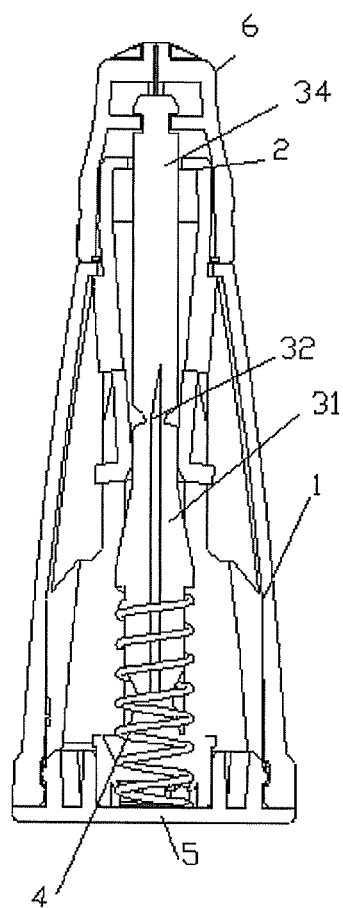
FIG. 2 is a structural view of the assembled blood lancet device according to one embodiment of the present invention.

As shown in FIGS. 1a, 1b and 2, the blood lancet device 100 further comprises an end cap 6, the blood lancet 3 further comprises a needle tip covering element 34, an end of such a needle tip covering element 34 extends to the outside of the housing 1, wherein, the internal structure of the end cap 6 is engaged with the end of the needle tip covering element 34 to cover the opening 11 with the end cap 6.

Figure 6A:
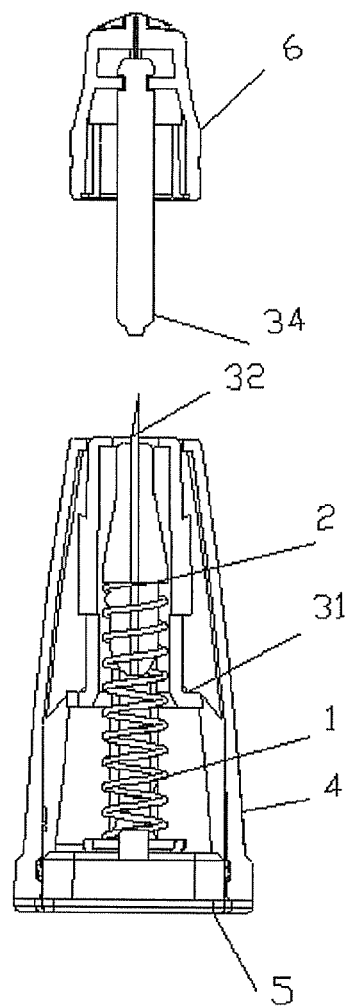
FIG. 6a-FIG. 6b are operational schematic views of the blood lancet device according to one embodiment of the present invention.
Figure 6B:
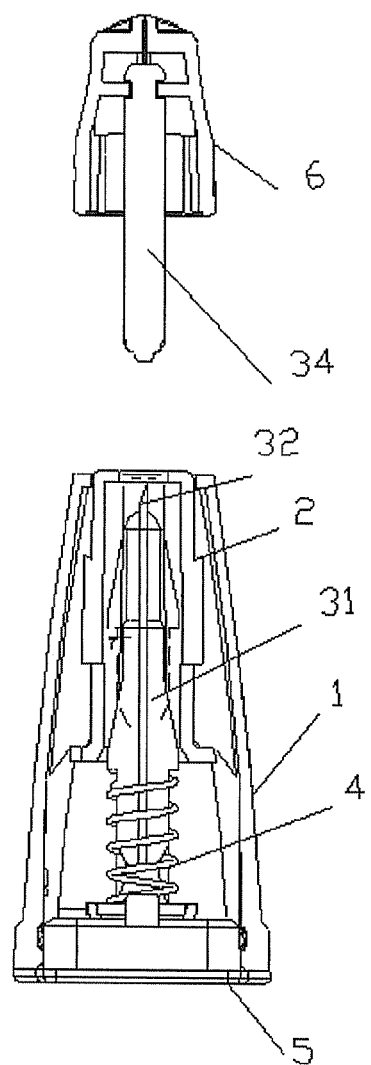

Hereafter, the operation processes of the blood lancet device 100 according to the present invention is described by referring to FIGS. 2, 6a and 6b.

FIG. 2 shows the state of the blood lancet device 100 after assembly. At this time, the biasing member 4 is under the pre-press state, and the recesses of the protruding portions 241, 242 on the guiding ends 23 of the sliding sleeve 2 are engaged with the guide rails inside the housing 1 so that the guiding ends 23 are pressed toward each other by the guide rails inside the housing, whereby the width of the guiding slot 22 is under a less state, such less width is smaller than the thickness of the lug 33 of the blood lancet 3, therefore, the lug 33 of the blood lancet 3 is pressed against the guiding end 23 of the sliding sleeve 2 by the biasing member 4.

FIG. 6a shows a schematic view of the blood lancet of the blood lancet device 100 under a piercing state. In order to operate the blood lancet 3, first, the end cap 6 is taken off, while the needle tip covering element 34 is removed. Then, said one end 21 of the sliding sleeve 2 is pressed. Based on such pressing, the sliding sleeve 2 is moved from up to down viewed from the figures, and then the engagement between the recesses on the protruding portions 241, 242 and the guiding portion inside the housing is released, so that the pressing forces applied on the guiding ends 23 are released, thereby, the guiding end 23 is restored to its normal position, for example the elastic non-deforming position shown in FIG. 4, due to the effect of the elasticity. Thus, the width of the guiding slot 22 is restored to be greater than the thickness of the lug 33 of the blood lancet 3, and at this time, the lug 33 of the blood lancet 3 is moved toward the opening 11 of the housing 1 along the guiding slot 22 under the action of the elasticity of the biasing member 4, so that the needle 32 of the blood lancet 3 is under the piercing state in which the needle tip 32 is exposed to the outside of the housing 1.

FIG. 6b shows a schematic view of the blood lancet of the blood lancet device 100 under the retraction state. After the blood lancet 3 is ejected, due to the resilience force of the biasing member 4, the blood lancet 3 is pulled back to the inside of the housing 1 by the biasing member 4. At this time, since the pawl 15 is provided at the pawl fitting slot 26 on the sliding sleeve and the opening 11, said one end 21 of the sliding sleeve 2 is always located at the outside of the housing 1.

It is noted that the slots 22 on the sliding sleeve 2 may not be served as the guiding slots along which the blood lancet 3 relatively slides relative to the sliding sleeve 2, but just allow the other end of the sliding sleeve to adapt to elastically deform radially and inwardly. In such a situation, when the other end of the sliding sleeve is pressed inside the housing so as to elastically deform radially and inwardly, the needle body 31 of the blood lancet abuts against the other end of the sliding slide 2 under the action of the biasing member 4; when the other end of the sliding slot 2 is not pressed inside the housing or subjects a less pressing force at the first position mentioned above, the needle body 31 is moved toward the opening along the sliding sleeve within the sliding sleeve under the action of the biasing member 4.

The number of the slot 22 can be one, two or more.

Although the embodiments of the present invention have been shown and described, it would be appreciated by those skilled in the art that many modifications, alterations and substitutions may be made in these embodiments without departing from the principles and spirit of the invention, the scope of which is defined in the claims and their equivalents.

The invention claimed is:

1. A blood lancet device, comprising:
    a housing provided with an opening at one end of the housing and guiding portions on an inner surface of the housing;
    a sliding sleeve having one end extending through said opening to an outside of the housing and the other end engaging with the guiding portions of the housing, the sliding sleeve being adapted to slide along an axial direction of said housing inside the housing;
    a blood lancet including a needle body and a needle tip disposed at one end of said needle body, said blood lancet adapted to move relative to said sliding sleeve so as to expose the needle tip at said opening; and
    a biasing member having one end engaged with the other end of the needle body,
    wherein said sliding sleeve is provided with at least one slot passing completely through a wall of the sliding sleeve, and the at least one slot extends toward said one end of the sliding sleeve from the other end of the sliding sleeve along a longitudinal axis of the sliding sleeve;
    wherein when the sliding sleeve is located at a first position within the housing, the other end of said sliding sleeve is pressed radially and inwardly by the guiding portions of the housing and elastically deformed radially and inwardly, such that the needle body is abutted against the other end of the sliding sleeve and is prevented from moving toward said opening of said housing;
    wherein when the sliding sleeve is moved to a second position within the housing, a pressing force applied on the other end of the sliding sleeve by the guiding portions is reduced or removed, such that said needle body is allowed to move toward said opening along said sliding sleeve under the action of the biasing member;
    wherein the other end of the sliding sleeve is configured to slide on the guiding portions and along a longitudinal axis of the housing during the first position to reach the second position;
    wherein said at least one slot includes two guiding slots extending toward said one end of the sliding sleeve from the other end of said sliding sleeve, said two guiding slots dividing said other end of the sliding sleeve into two guiding ends which can elastically deform toward each other;
    wherein said needle body also includes two lugs arranged in opposite, said two lugs are adapted to move along said two guiding slots under the action of the biasing member;
    wherein engagements between said guiding portions and said guiding ends are adapted to press two guiding ends so as to reduce the width of the guiding slots at said other end of the sliding sleeve to prevent said two lugs from moving toward said one end of said sliding sleeve along said two guiding slots under the action of the biasing member;
    wherein a tip end of each guiding end has a protrusion protruding radially and outwardly, and said protrusion is adapted to engage with said guiding portions; and
    wherein during movement of the sliding sleeve from the first position to the second position, the protrusion is continuously engaged and pressed radially and inwardly by said guiding portions such that when the sliding sleeve is at the second position, the protrusions move away from the lugs in a radial direction so that said lugs move up along said two guiding slots under the action of the biasing member.

2. The blood lancet device according to claim 1, wherein:
    a recess is provided on said protrusion, and said guiding portion is a guide rail extending along the axial direction of the housing, said recess is fitted with said guide rail.

3. The blood lancet device according claim 2, wherein:
an initial section of said guide rail fitted with said recess is formed into an inclined engaging surface.

4. The blood lancet device according to claim 1, wherein:
said guiding portion comprises a sliding slot extending along the axial direction of the housing, said protrusion is adapted to move along said sliding slot.

5. The blood lancet device according to claim 1, wherein:
a groove extending toward said one end of the sliding sleeve from the tip end of the guiding end is provided on each guiding end, and said groove divides the corresponding protrusion into a first protruding portion and a second protruding portion which are separated.

6. The blood lancet device according to claim 5, wherein:
said guiding portions comprise a first guiding slot portion and a second guiding slot portion extending along the axial direction of the housing, and said first protruding portion and said second protruding portions are adapted to move along said first guiding slot portion and said second guiding slot portion, respectively.

7. The blood lancet device according to claim 5, wherein:
a first recess is provided on said first protruding portion and a second recess is provided on said second protruding portion, and said guiding portion includes a first guide rail and a second guide rail which are respectively fitted with said first recess and said second recess and extend along the axial direction of the housing.

8. The blood lancet device according to claim 7, wherein:
initial sections of said first guide rail and said second guide rail respectively fitted with said first recess and said second recess are formed as inclined engaging surfaces.

9. The blood lancet device according to claim 1, wherein:
an outer surface of each guiding end is provided with a longitudinal rib protruded radially and outwardly, said guiding portion comprises a rib guiding slot extending along the axial direction of the housing, and said longitudinal rib is adapted to engage with said rib guiding slot.

10. The blood lancet device according to claim 9, wherein:
a thickness of the longitudinal rib in the radial direction is gradually reduced in the direction from said other end of the sliding sleeve to said one end of the sliding sleeve.

11. The blood lancet device according to claim 9, wherein:
said longitudinal rib defines a distance by which said one end of the sliding sleeve moves to the outside of the opening.

12. The blood lancet device according to claim 1, wherein:
an end of each lug which enters in the guiding slot has a tapered shape which is tapered toward said one end of the needle body.

13. The blood lancet device according to claim 12, wherein:
the end of each lug which enters in the guiding slot forms said tapered shape in a manner of having an inclined surface or a semi-cylindrical surface.

14. The blood lancet device according to claim 1, wherein:
an end cover is provided at the other end of said housing, the other end of said biasing member is fixed on said end cover.

15. The blood lancet device according to claim 1, wherein:
said blood lancet device further comprises an end cap;
said blood lancet further comprises a needle tip covering element having an end extending to the outside of the housing,
wherein, an internal structure of said end cap is engaged with an end of said needle tip covering element so as to cover said opening with said end cap.

16. The blood lancet device according to claim 1, wherein:
a lug guiding element extending along the axial direction of the housing is also provided inside the housing.

17. The blood lancet device according to claim 1, wherein:
at least one stopper is further provided at an outer surface of the sliding sleeve, said stopper defines a distance by which said one end of the sliding sleeve move to the outside of the opening.

18. The blood lancet device according to claim 1, wherein:
an interference fitting is formed between the opening of said housing and the outer surface of said one end of the sliding sleeve to prevent said one end of the sliding sleeve from sliding into the inside of the housing.

19. The blood lancet device according to claim 1, wherein:
a pawl is provided in the vicinity of said opening inside said housing, and a pawl fitting slot is provided at the tip end of said one end of the sliding sleeve, the fitting between the pawl and the pawl fitting slot prevents said one end of the sliding sleeve from sliding into the inside of the housing.

* * * * *